United States Patent
Sogard et al.

(10) Patent No.: US 6,699,276 B2
(45) Date of Patent: *Mar. 2, 2004

(54) SUPPORT STRUCTURE/MEMBRANE COMPOSITE MEDICAL DEVICE

(75) Inventors: David Sogard, Edina, MN (US); Susan Shoemaker, Elk River, MN (US); Scott R. Smith, Chaska, MN (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/505,158

(22) Filed: Feb. 16, 2000

(65) Prior Publication Data

US 2002/0045931 A1 Apr. 18, 2002

Related U.S. Application Data

(62) Division of application No. 08/721,834, filed on Sep. 26, 1996, now abandoned.

(51) Int. Cl.⁷ .................................................. A61F 2/06
(52) U.S. Cl. .................. 623/1.13; 623/1.44; 156/547; 156/294
(58) Field of Search ........................... 623/1.13, 1.44, 623/1.46, 901; 156/547, 294

(56) References Cited

U.S. PATENT DOCUMENTS

| | | |
|---|---|---|
| 3,657,744 A | 4/1972 | Ersek |
| 4,300,244 A | 11/1981 | Bokros |
| 4,409,172 A | 10/1983 | Ward, Jr. et al. |
| 4,503,569 A | 3/1985 | Dotter |
| 4,580,568 A | 4/1986 | Gianturco |
| 4,604,762 A | 8/1986 | Robinson |
| 4,731,073 A | 3/1988 | Robinson |
| 4,732,152 A | 3/1988 | Wallstén et al. |
| 4,733,665 A | 3/1988 | Palmaz |
| 4,798,606 A | 1/1989 | Pinchuk |
| 4,816,339 A | 3/1989 | Tu et al. |
| 4,850,999 A | 7/1989 | Planck |

(List continued on next page.)

FOREIGN PATENT DOCUMENTS

| | | |
|---|---|---|
| EP | 0 539 237 | 4/1993 |
| EP | 0 657 147 | 6/1995 |
| EP | 0 938 879 A2 | 9/1999 |
| SU | 1457 921 | 2/1989 |
| WO | WO 95/05132 | 2/1995 |

(List continued on next page.)

OTHER PUBLICATIONS

Percutaneous Endovascular Graft: Experimental Evaluation by David D. Lawrence, Jr., M.D., Chuslip Charnsangavej, M.D., Kenneth C. Wright, Ph.D., Cesar Gianturco, M.D., Sidney Wallace, M.D., Radiology, May 1987, pp. 357–360.

*Primary Examiner*—Bruce Snow
(74) *Attorney, Agent, or Firm*—Hoffmann & Baron, LLP

(57) ABSTRACT

The present invention relates to a support structure/membrane composite device which includes a support structure, such as a radially expandable stent, a porous non-textile polymeric membrane adjacent to said stent and a thermoplastic anchor means attaching said stent to said porous non-textile polymeric membrane. The porous non-textile polymeric membrane is preferably made from expandable fluoropolymer materials. The anchoring means is a thermoplastic material which is dissolvable at the interface between the support structure and membrane by a suitable solvent which wets the membrane surface and deposits the thermoplastic material within the pores of the membrane. Methods of preparing the device are also disclosed.

21 Claims, 3 Drawing Sheets

U.S. PATENT DOCUMENTS

| | | | |
|---|---|---|---|
| 4,856,516 | A | 8/1989 | Hillstead |
| 4,857,069 | A | 8/1989 | Kira |
| 4,886,062 | A | 12/1989 | Wiktor |
| 4,925,710 | A | 5/1990 | Buck et al. |
| 5,078,726 | A | 1/1992 | Kreamer |
| 5,084,065 | A | 1/1992 | Weldon et al. |
| 5,116,360 | A | 5/1992 | Pinchuk et al. |
| 5,123,917 | A | 6/1992 | Lee |
| 5,163,951 | A | 11/1992 | Pinchuk et al. |
| 5,175,052 | A | 12/1992 | Tokuda et al. |
| 5,282,824 | A | 2/1994 | Gianturco |
| 5,330,500 | A | 7/1994 | Song |
| 5,366,504 | A | 11/1994 | Andersen et al. |
| 5,383,926 | A | 1/1995 | Lock et al. |
| 5,389,106 | A | 2/1995 | Tower |
| 5,443,499 | A | 8/1995 | Schmitt |
| 5,466,509 | A | 11/1995 | Kowligi et al. |
| 5,474,727 | A | 12/1995 | Perez |
| 5,507,771 | A | 4/1996 | Gianturco |
| 5,522,881 | A | 6/1996 | Lentz |
| 5,562,697 | A | 10/1996 | Christiansen |
| 5,562,728 | A | 10/1996 | Lazarus et al. |
| 5,591,195 | A | 1/1997 | Taheri et al. |
| 5,620,763 | A | 4/1997 | House et al. |
| 5,637,113 | A * | 6/1997 | Tartaglia et al. ............ 623/1 |
| 5,653,697 | A | 8/1997 | Quiachon et al. |
| 5,674,241 | A | 10/1997 | Bley et al. |
| 5,700,285 | A | 12/1997 | Myers et al. |
| 5,713,917 | A | 2/1998 | Leonhardt et al. |
| 5,718,973 | A | 2/1998 | Lewis et al. |
| 5,735,892 | A | 4/1998 | Myers et al. |
| 5,749,880 | A | 5/1998 | Banas et al. |
| 5,810,870 | A | 9/1998 | Myers et al. |
| 5,906,641 | A | 5/1999 | Thompson et al. |
| 5,925,074 | A | 7/1999 | Gingras et al. |
| 5,925,075 | A | 7/1999 | Myers et al. |
| 5,928,279 | A * | 7/1999 | Shannon et al. ............ 623/1 |

FOREIGN PATENT DOCUMENTS

| | | |
|---|---|---|
| WO | WO 95/05555 | 2/1995 |
| WO | WO 95/29647 | 11/1995 |
| WO | WO 96/00103 | 1/1996 |
| WO | WO 96/03092 | 2/1996 |
| WO | WO 96/10967 | 4/1996 |
| WO | WO 96/22745 | 8/1996 |
| WO | WO 96/26689 | 9/1996 |
| WO | WO 98/00090 | 1/1998 |

* cited by examiner

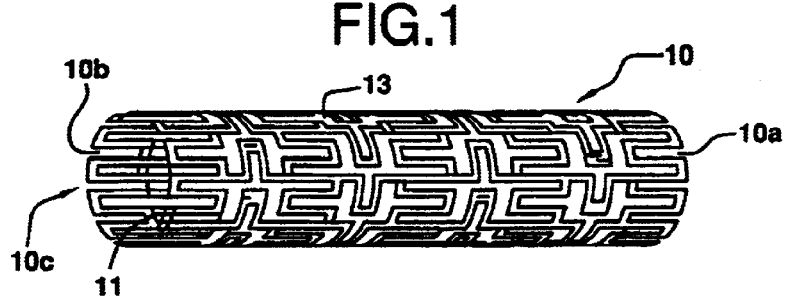
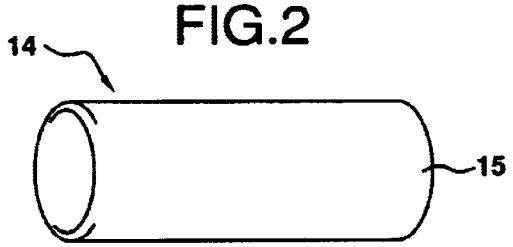
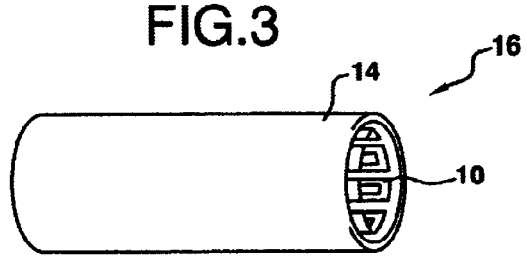
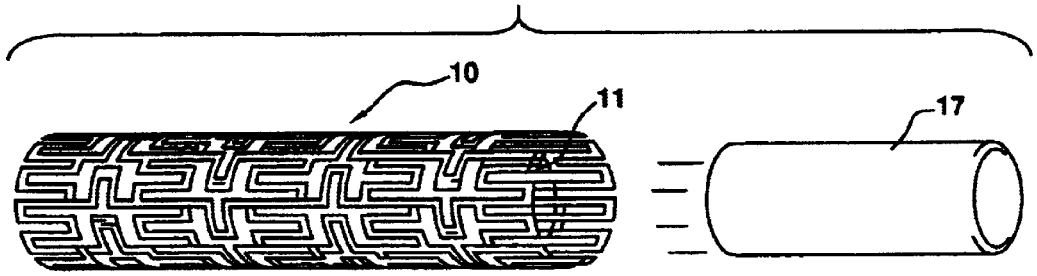

SUPPORT STRUCTURE/MEMBRANE COMPOSITE MEDICAL DEVICE

The present application claims priority to and is a divisional application of application U.S. Ser. No. 08/721,834, filed Sep. 26, 1999 now abandoned.

FIELD OF THE INVENTION

The present invention relates generally to an implantable intraluminal device. In its broadest aspect, the present invention relates to a means of attaching porous, non-textile polymeric membranes to a support structure, scaffold or framework. More particularly, the present invention relates to a composite intraluminal device including a support structure or framework, such as a stent, in combination with a porous membrane covering or liner.

BACKGROUND OF THE INVENTION

It is well known to employ various endoprostheses for the treatment of diseases of various body vessels. One type of endoprostheses is commonly referred to as a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures or aneurysms in various blood vessels. These devices are implanted within the vessel to open and/or reinforce collapsing or partially occluded sections of the vessel. Often, stents may be used in conjunction with a graft with provides additional support for blood flow through weakened sections of the blood vessel.

Stents generally are open ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessels. The stent is generally inserted in a radially compressed state and expanded either through a self-expanding mechanism, or through the use of balloon catheters. For example, various stent constructions and their method of deployment are shown in U.S. Pat. No. 4,503,569 to Dotter; U.S. Pat. No. 4,733,665 to Palmaz; U.S. Pat. No. 4,856,561 to Hillstead; U.S. Pat. No. 4,580,568 to Gianturco; U.S. Pat. No. 4,732,152 to Wallsten and U.S. Pat. No. 4,886,062 to Wiktor. Published PCT Application No. PCT/US 95/08975, based on U.S. priority applications U.S. Ser. Nos. 08/282,181 and 08/457,354, also discloses a tubular shaped stent which is inflatable by balloon and which shrinks minimally in the longitudinal direction during expansion. The foregoing PCT publication and its U.S. priority applications, and the aforementioned U.S. patents are incorporated herein by reference. Additionally, published PCT Application WO 96/26689, entitled "Improved Longitudinally Flexible Expandable Stent" and being based on U.S. priority application Ser. Nos. 08/396,569 filed Mar. 1, 1995 and Ser. No. 08/511,076 filed Aug. 3, 1995 also discloses stents useful in the present invention, both this PCT Application and its U.S. priority applications being incorporated by reference herein.

The attachment of stents to grafts for use in endovascular applications has generally been by means of sutures, cuffs or pockets in the graft which serve to house the stent. For example, U.S. Pat. No. 5,522,881 discloses cuffs on the exterior surface of the graft which serve as open pockets into which stents can be placed. It is known to attach stents to grafts using sutures. For the most part, grafts which are used in combination with stents as composite device have been made from textile materials, which are woven, knitted or braided.

Composite devices made from stents and films have been disclosed in the art. For example, U.S. Pat. No. 5,123,916 to Lee describes an expandable intraluminal vascular graft which includes concentric cylindrical tubes having a plurality of scaffold members mounted therebetween. The scaffold members are expandable, ring-like and provide circumferential rigidity to the graft.

U.S. Pat. No. 5,383,926 to Lock, et al. describes a radially expandable endoprosthesis which comprises an elongated sleeve member in which the radially outward expansion of the sleeve is limited by connecting strips. These strips are selectively removable to allow further outward expansion. The sleeve can be C-shaped in cross-section to allow for further expanded growth. The sleeve member generally has an open wall structure such as those typical of wire mesh tubing or slotted tubing. An expandable sheet material may be disposed across the open region of the C-shaped sleeve member and may be formed of Goritex®.

U.S. Pat. No. 5,389,106 to Tower discloses an impermeable expandable intravascular stent. An impermeable deformable membrane interconnects portions of a distensible frame to form an impermeable exterior wall to the frame. The membrane is formed of a synthetic non-latex, non-vinyl polymer and the frame is made from a fine wire of annealed platinum. The distensible frame may be an expandable stent and the membrane is a hypoallergenic biologically inert material that is free of latex rubber proteins. The membrane should be impermeable and have the properties of elasticity, distensibility and barrier protection. No specific classes of materials are mentioned except the product name Tactylon®. The impermeable membrane is attached to the stent by dipping the stent into the polymer solution of the membrane and subsequently drying the device to remove the solvent. The stent is imbedded within the membrane surface.

With respect to grafts made from extruded materials such as ePTFE, the use of sutures to attach such grafts encounters problems of dealing with bleeding through suture holes, since these expanded fluoropolymer materials do not generally have the self-sealing capability of elastomeric materials. Additionally, ePTFE is inherently resistant to adhesive bonding and few biocompatible adhesives will bond to its surface. While this inherent surface characteristic of ePTFE has advantages because it imparts a natural anti-thrombogenic characteristic to the surface of grafts made therefrom, it has been heretofore difficult to attach stents to grafts made from ePTFE without encountering the foregoing problems. The present invention seeks to overcome difficulties of attaching ePTFE material to a stent by using an anchoring material which can be carried into and entrapped in the porous surface of ePTFE.

In certain applications, it is necessary to protect against excessive cell growth through the stent (intimal hypoplasia), as well as thrombus formation and plaque buildup in the vascular system. In the bile or urogenital tract regions, tumor growth is also of concern. Additionally, arterial build-up of plaque and other debris can become dislodged from the vessel surface during or subsequent to implantation of the stent. To prevent such occurrences, the use of a cover or liner in combination with an ePTFE stent has been suggested by the co-pending U.S. application Ser. No. 09/691,782 filed concurrently herewith and entitled "Improved Covered Stent". This copending application describes the use of unsintered ePTFE as a cover or liner used for a radially expandable stent. This co-pending application is herein incorporated by reference. In the present application, a means of attaching such a cover or liner to a stent is provided.

SUMMARY OF THE INVENTION

In one embodiment of the invention, a support member/membrane composite device is provided, which device includes a support structure such as a radially expandable stent, a porous polymeric non-textile membrane adjacent to said support structure to define an interface therebetween; and a thermoplastic anchor means attached to and extending from said stent into said porous polymeric non-textile membrane at said interface to anchor the membrane to the support structure. The porous polymeric non-textile membrane may be selected from a variety of extruded materials such as ePTFE, polyurethane, polyimides and the like. The support structure can be essentially any medical device which is useful in or on the body. More preferably, the support structure is designed for use in the body, such as in intraluminal applications. Most preferably the support structure takes the form of a radially expandable stent.

The radially expandable stent may be chosen from a wide variety of stent materials and configurations. For example, the stent may be self-expandable, balloon expandable or made from a memory alloy, the configuration of which can be controlled by temperature. A thermoplastic anchoring material is attached to the stent and penetrates into the porous surface of the membrane. Penetration is accomplished without deleteriously interfering with the structural integrity of the membrane by dissolving a portion of the anchoring material at the support structure/membrane interface such that the dissolved material penetrates the pores of the membrane. The solvent is then removed, leaving the anchoring material to resolidify and form an anchoring means within the microporous membrane structure.

The support structure may be completely covered by a conformal coating of the anchoring material or it can be coated at selected, predetermined portions of the support structure which contact the membrane. For example, if the support structure is a stent, the stent may be completely or partially covered by the anchoring material.

The present invention further relates to a method of making an implantable support structure/membrane composite device, and preferably a tubular device, which includes the steps of providing a support structure; coating at least a portion of said support structure with a thermoplastic anchoring material; and positioning a biocompatible porous non-textile polymeric membrane in intimate contact with said anchoring material to form an interface therebetween. Further, this method includes the steps of dissolving with a suitable solvent at least a portion of said anchoring material at the support structure/membrane interface to cause penetration of said anchoring material into the porous membrane; and removing the solvent to allow resolidification of the anchoring material within the porous membrane, thereby anchoring said support structure to said porous membrane. In a preferred embodiment, the support structure is an expandable structure for intraluminal applications and most preferably a radially expandable stent.

BRIEF DESCRIPTION OF THE DRAWINGS

FIG. 1 is a perspective showing a slotted radially expandable tubular stent which may be used in the support structure/membrane composite device of the present invention.

FIG. 2 is a perspective showing a porous non-textile tubular membrane of the type which may be used in the composite device of the present invention.

FIG. 3 is perspective showing the support structure/membrane composite of the present invention. Wherein the support structure is a radially expandable stent.

FIG. 4 is a perspective showing a porous non-textile tubular support structure and membrane liner used in the composite device of the present invention.

DETAILED DESCRIPTION OF THE PREFERRED EMBODIMENTS

Figure 5:
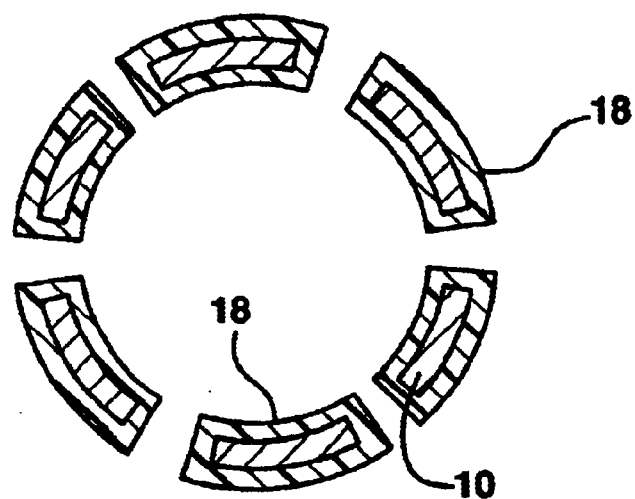
FIG. 5 is a schematic sectional end view of a stent of the type of which may be used in the present invention showing a conformal coating as the anchoring material.

The present invention provides a means of attaching a liner or a cover to a support structure and particularly to a stent for implantation intraluminally within a body vessel and disposed adjacent an occluded, weakened or damaged portion of the vessel, so as to maintain the patency of the vessel and prevent excessive ingrowth and dislodging of plaque or debris from the vessel wall from filtering into the blood stream. The support structure/membrane composite device is typically delivered intraluminally via a balloon catheter. The device is delivered in a compressed condition and once properly positioned may be deployed by radially expanding the stent. Although one of the most common means of deploying such an intraluminal device is by balloon expansion, the present invention also includes self-expanding stents such as spring-biased stents and those which are formed from superelastic shaped memory alloy materials such as nitinol.

The liner or covering is hereinafter described as a membrane. The term "membrane" as used herein is meant to include a non-woven polymeric material in the form of a tube or sheet which can serve as a covering or liner for the stent and which has a porous surface sufficient to allow the dissolvable anchoring material of the present invention to penetrate and resolidify. The membrane material must be a biocompatible and hemocompatible polymeric material which although porous, is substantially fluid-tight and allows for a certain amount of neointima growth such that it is assimilated and well accepted in the vessel. Pore size is of particular importance in the present invention and disqualifies a number of materials which are not sufficiently porous to allow anchoring and tissue ingrowth to occur. Other membrane characteristics such as compliance, flexibility and fluid-tightness are also important to many contemplated applications of the present invention.

The non-woven polymeric membrane material may be formed by any conventional method provided the method allows for a porous surface structure to remain or be created. For example, extrusion processes such as ram extrusion; polymeric casting techniques such as solvent casting and film casting; molding techniques such as blow molding, injection molding and rotational molding; and other thermoforming techniques useful with polymeric materials may be employed and chosen to best serve the type of material used and specific characteristics of the membrane desired.

Expanded polytetrafluoroethylene (ePTFE) is well known for its use in vascular grafts and endoprostheses. This material is, however, difficult to attach to other articles because of its natural resistance to adhesive bonds. The present invention seeks to take advantage of the controllable pore size of ePTFE by using the node and fibril structure as a means to incorporate the anchoring material therewithin. Thus, the preferred membrane material of the present invention is ePTFE, although other thermoformable polymeric materials such as porous polyurethane and the like may be employed.

The porous membranes of the present invention need not be structurally sufficient per-se to withstand the pressures of blood flow and may be used merely as thin covers or liners for the stents and other devices in applications where dislodging of plaque debris and/or regrowth of the occlusion through the stent wall is of concern. Thus, in one embodiment, the membrane may have the structural integrity of a typical endoprothesis or vascular graft, and in another embodiment the membrane may be of a thinner wall thickness than a typical vascular graft, but sufficient in thickness to serve as a prophylactic liner or cover against the aforementioned debris.

The anchoring material may be selected from a wide variety of bio- and hemo-compatible thermoplastic materials which can be applied to the support structure surface, e.g., at the support structure/membrane interface and partially dissolved to penetrate into the porous membrane surface. Certain thermoplastic materials, such as nylon, acrylics, polyethylene and the like are not readily dissolvable by solvents which are suitable for the present invention. The solvents used in the present invention must be capable of wetting the membrane surface and penetrating the pores. In the case of ePTFE membranes, wettability of the surface is difficult to accomplish due to the surface tension properties of the fluoropolymeric structure. Many solvents will not readily wet the surface of ePTFE sufficiently to penetrate the pores. Thus, the choice of anchoring material and solvent must be made with these properties in mind. The anchoring material must be sufficiently dissolvable or softened at the interface to flow and penetrate into the membrane pores.

Among those materials which are useful in the anchoring means include, without limitation, polyurethanes, silicones and bioresorbable polymers. Mixtures of these materials are also contemplated. Polyurethanes are the preferred material because they are biocompatible, readily solvated and structurally strong. Polyether polyurethanes and polycarbonate polyurethanes are among the polyurethanes contemplated. Polyurethane having pendent bio-active agents are also useful. For example, a segmented, aromatic, polycarbonate-based polyurethane material which is commercially available and sold under the trade name Chronoflex AR, manufactured by Cardio Tech International, a subsidiary of Polymedica Industries, is an example of one useful polyurethane. Useful silicone materials include polydimethylsiloxane and the like.

Among the bio-resorbable materials which are useful include various polymers and co-polymers of poly(glycolic acid) (PGA), poly(lactic acid) (PLA), polydioxanoes, polyoxalates, poly($\alpha$-esters), polyanhydrides, polyacetates, polycaprolactones, poly(orthoesters), and the like. Stereopolymers of L- and D-lactic acid are also useful. Useful copolymeric materials include the copolymers of bis(p-carboxyphenoxy) propane acid and sebacic acid, sebacic acid copolymers, copolymers of carprolactone, poly(lactic acid)/poly(glycolic acid)/polyethyleneglycol copolymers, copolymers of polyurethane and poly (lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof Binary and ternary systems are contemplated. Mixtures of the above mentioned polymers and copolymers are also contemplated.

As previously described, the anchoring materials are applied to the surface of the support structure, i.e., a stent, such that when the stent and membrane are positioned adjacent to each other the anchoring material is present at the interface between the two. The anchoring material may be applied to the stent by any well known method, including dipping, spraying, brushing and the like. Alternatively, the coating may be applied by various plasma deposition techniques well known in the art. The anchoring material may take the form of a conformal coating about the stent and may cover some of or all of the stent, but must be present on at least a portion of the stent which is present at the stent/membrane interface.

As previously mentioned, the support structure of the composite device may be chosen from a wide variety of materials and configurations. Endovascular stents are the preferred support structure and may be formed in a wide variety of configurations. An example of a useful stent in the present invention is shown in FIG. 1. This particular stent represents a slotted tubular stent which is designed to radially expand either by balloon catheter or by forming the stent from a temperature-sensitive memory alloy which changes shape at a designated temperature or temperature range. Other stent types, such as tubular-shaped wire stents and self-expandable spring-biased stents are also contemplated. The stent may be made from a variety of materials including stainless steel, titanium, platinum, gold and other bio-compatible metals. Thermoplastic materials which are inert in the body may also be employed. Shaped memory alloys having superelastic properties generally made from specific ratios of nickel and titanium, commonly known as nitinol, are among the preferred stent materials.

Referring now to the figures, FIG. 1 shows a slotted tubular stent 10 which may be formed of the aforementioned materials and used in the present support structure/membrane composite device 16. FIG. 2 represents a tubular membrane 14 of the present invention which can be used as either a liner or covering for the stent. The membrane need not be formed in tubular form but can be made from an extruded sheet of material which can be wrapped around all or a portion of the stent to form a cover or liner. For example, a sheet membrane may be first formed and wrapped externally about the stent and seamed along the longitudinal axis to form a cover. Such a sheet may be made with a high degree of uniaxial orientation. The relative axis of orientation of the stent may vary depending on the membrane material used and orientation and size of its pore structure. For example, in applicants' aforementioned copending application (760-3), the extruded membrane may be formed from unsintered ePTFE sheets which have been expanded longitudinally and aligned generally longitudinally along the longitudinal stent axis, transverse to the longitudinal direction, or in an off-axis angle therebetween. In another example, ePTFE membrane may be stretched and sintered several times to create a preformed ePTFE having expansion memory, such as shown in PCT Publication No. WO 96/00103 (Application No. U.S. 95/07,326), which is herein incorporated by reference. This publication is based on U.S. priority application Ser. No. 08/265,794, filed Jun. 27, 1994, which is also herein incorporated by reference. The preformed ePTFE allows for further expansion once the stent is implanted and radially deployed.

Turning now to the method of preparing the composite structure, a chosen stent is provided and coated by one of the aforementioned methods with the anchoring material. For example, a nitinol stent having the tubular, slotted structure as represented by FIG. 1, may be coated with a conformal coating of the anchoring material, for example polyurethane. Stent 10 is generally an elongate tube having opposed open ends 10a and 10b and a central lumen 10c extending therebetween. Stent 10 has an open slotted body defined by an interior surface 11 and an opposed exterior surface 13. The open construction of stent 10 provides for longitudinal flexibility as well as the ability to radially expand.

Figure 6:
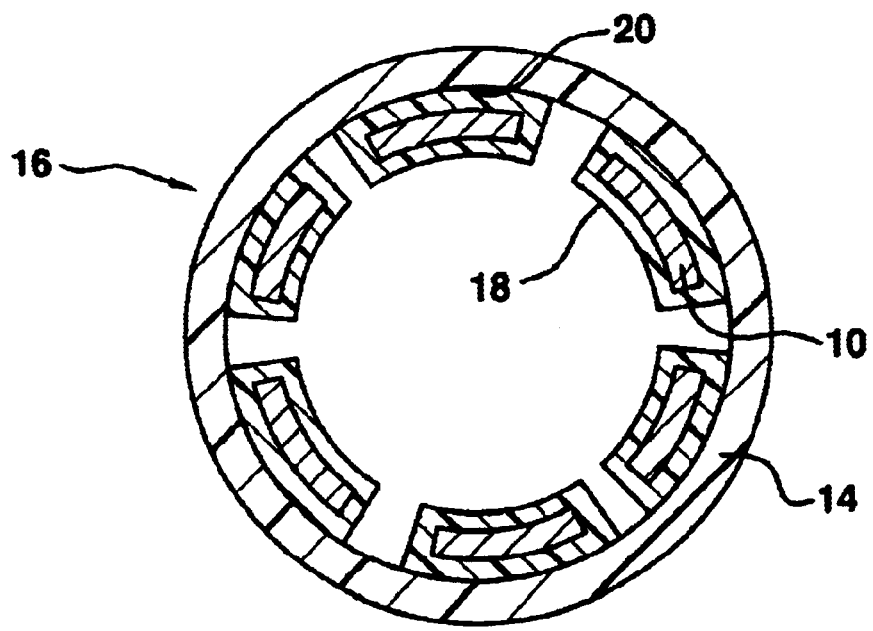
FIG. 6 is a schematic sectional end view of the conformally coated stent of FIG. 5 having the membrane cover disposed circumferentially therearound.

Prior to applying membrane 14 (FIG. 2) to stent 10 to form the composite device 16 (FIG. 3), in the preferred embodiment shown herein, stent 10 is conformally coated with an anchoring material 18. As shown in FIGS. 5 and 6, material 18 completely surrounds stent 10. Thus upon applying membrane 14 to coated stent 10 an interface 20 is defined between the anchoring material 18 and member 14.

Figure 7:
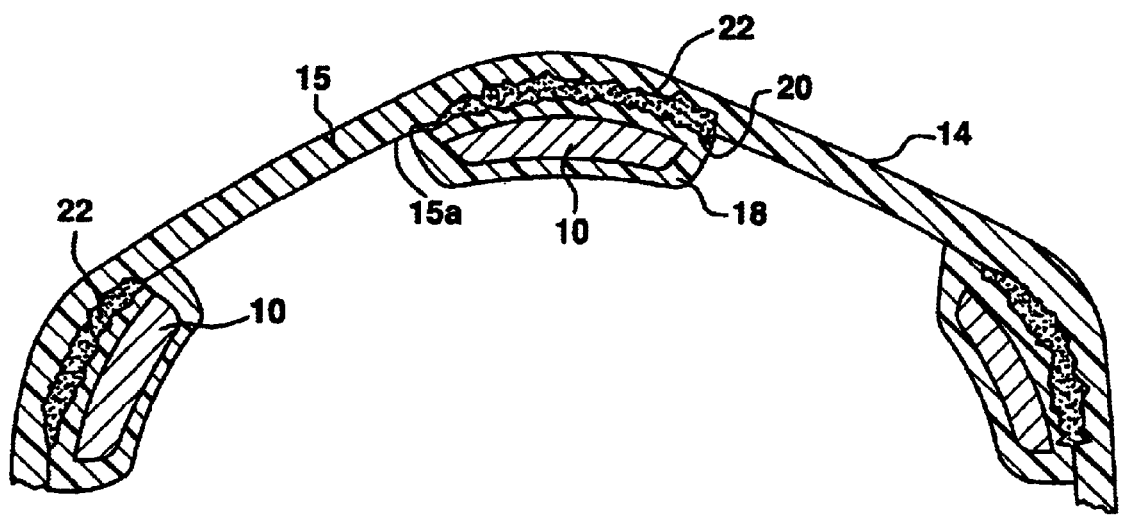
FIG. 7 is an enlarged cross-sectional view of the stent/membrane interface showing the conformally coated stent anchored to the membrane.

Referring additionally to FIG. 7, interface 20 is shown as the area where an inner surface 15a of porous membrane 14 is in intimate contact with the conformal coating anchoring material 18. The anchoring material 18 penetrates the porous surface 15 of membrane 14 through inner surface 15a. The adjacent location forms a penetration area 22 whereby the conformal coating anchoring material 18 has penetrated the porous surface 15 of the membrane and resolidified subsequent to removal of the solvent.

The solvent may be applied at the interface 20 either just prior to placing the membrane 14 in contact with the stent 10 coated with the anchoring material 18, or alternatively the solvent can be applied at the desired interface locations subsequent to positioning the stent and the membrane relative to one another.

Figure 8:
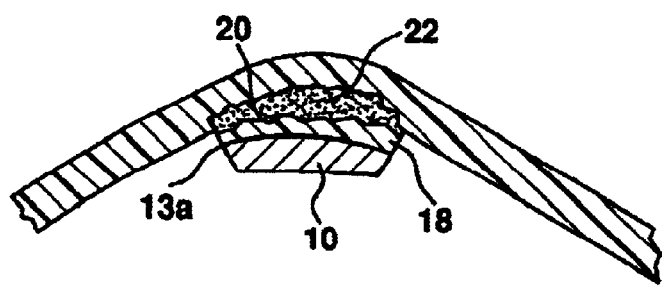
FIG. 8 is an enlarged cross-sectional view of the stent/membrane interface where the anchoring material is only partially covering the stent.

FIG. 8 shows an enlarged schematic view of the composite device whereby stent 10 is only partially coated by anchoring material 18. In the embodiment of FIG. 8, the anchoring material 18 is deposited only on exterior surface portions 13a, at the interface 20 between stent 10 and the porous surface 15 of membrane 14. It is contemplated that such selective depositing can be provided over the entire exterior surface 13 or only at intermittent exterior locations.

As previously mentioned, the wettability of the membrane is essential to proper anchoring of the stent, particularly when the membrane is formed of a hydrophobic, adhesive resistant material such as ePTFE. As discussed above, the type of solvent employed must be both capable of dissolving the anchoring material and of wetting the surface of the membrane. Suitable solvent materials, which have been found to be useful with polyurethane anchoring materials and ePTFE membranes include, without limitation, dimethylacetamide, tetrahydrofuran, ethers, methylene chloride, chloroform, toluene and mixtures thereof A mixture of dimethylacetamide and tetrahydrofuran has been found to be particularly useful in combination with ePTFE membranes and polyurethane anchoring materials. This mixture provides a balance of wetting and solvent properties which are particularly effective at causing penetration and entrapment of the anchoring material within the pores of the ePTFE.

Other solvents may be employed provided they are capable of wetting the membrane, i.e., ePTFE surface, i.e., reducing surface tension such that the anchoring material will flow into the porous microstructure, and are capable of sufficiently dissolving the anchoring material at the support structure/membrane interface to cause flow and penetration into the membrane. The present process is distinct from conventional solvent welding by the fact that no dissolving of the membrane is intended. Rather, the solvents chosen should have little or no effect on the membrane and serve only as a means to infiltrate the microstructure and carry the anchoring material therewith. The solvents are then removed by evaporation and the anchoring material is permitted to dry and resolidify within the porous structure. Thus, a new interface is formed at penetration area 22 which represents domains anchoring material within the ePTFE pores, i.e., the pores of the membrane have been at least partially filled with the solid anchoring material.

Various bioeffecting agents may also be included in the pores of the membrane by well known methods. For example, anti-infective agents and/or antithrombogenic agents may be coated on the membrane or disposed within some of the pores of the membrane prior to implantation. Additionally, such bioeffecting agents may also be employed on the stent or in the anchoring material used thereon. One example is shown in commonly assigned International Patent Application No. W095/29647, published on Nov. 9, 1995 and its U.S. priority Applications Serial No. 235,300, filed Apr. 29, 1994, and Serial No. 350,233, filed Dec. 1, 1994, which are incorporated herein by reference.

Stent 10 may be employed in combination with a member 14 as shown in FIGS. 1 and 2. Membrane 14 may be applied, in a preferred embodiment, over tubular stent 10 so as to fully circumferentially surround stent 10. While the preferred embodiment contemplates employing member 12 about the exterior surface 13 of stent 10 as shown in FIG. 3, it is also contemplated that a membrane 17 in the form of a liner may be placed about the interior surface 11 of stent 10 such as shown in FIG. 4. The membrane 14 thereby forms an effective barrier about stent 10 preventing excessive cell or tissue ingrowth or thrombus formation through the expanded wall of tubular stent 10.

Various changes in modifications may be made to the invention, and it is intended to include all such changes and modifications as come within the scope of the invention and as set forth in the following claims.

What is claimed is:

1. A method of making an implantable support structure/membrane composite medical device comprising the step of:
    (i) providing a support structure;
    (ii) coating at least a portion of said support structure with a thermoplastic anchoring material;
    (iii) positioning a porous non-textile polymeric membrane in intimate contact with said anchoring material to form an interface therebetween;
    (iv) dissolving with a suitable solvent at least a portion of said anchoring material at said interface to cause penetration of said anchoring material into said porous non-textile polymeric membrane; and
    (v) removing said solvent to allow resolidification of said anchoring material within said porous non-textile polymeric membrane, thereby anchoring said support structure to said porous non-textile polymeric membrane.

2. The method of claim 1 wherein said thermoplastic anchoring material is selected from the group consisting of polyurethanes, silicones, bioresorbable polymers and mixtures thereof.

3. The method of claim 1 wherein said solvent is a wetting agent for said porous non-textile polymeric membrane.

4. The method of claim 1 wherein said solvent is selected from the group consisting of dimethylacetamide, tetrahydrofuran, ether, chloroform, methylene chloride, toluene, and mixtures thereof.

5. The method of claim 1 wherein said porous non-textile polymeric membrane is selected from the group consisting of fluoropolymers, polyurethanes and polyimides.

6. The method of claim 5 wherein said porous non-textile polymeric membrane is ePTFE.

7. The method of claim 6 wherein said porous non-textile polymeric membrane is a pre-formed ePTFE.

8. The method of claim 1 wherein said support structure is a material selected from the groups consisting of biocompatible metals and thermoplastic polymers.

9. The method of claim 8 where in said support structure is a stent.

10. The method of claim 9 wherein said stent is radially expandable by a balloon catheter or by a self-expanding mechanism.

11. The method of claim 10 wherein said stent is made from nitinol.

12. A method of anchoring an endovascular stent to a porous biocompatible fluoropolymer membrane comprising the steps of:
   (i) providing a radially expandable endovascular stent having a solid thermoplastic anchoring material on its surface;
   (ii) positioning said porous biocompatible fluoropolymer membrane in intimate contact with said anchoring material to form an interface therebetween;
   (iii) applying a suitable solvent for said anchoring material which wets said fluoropolymer membrane surface to cause flow of at least a portion of said anchoring material into said porous biocompatible membrane;
   (iv) removing said solvent to resolidify said anchoring material within said porous biocompatible membrane, thereby anchoring said stent to said membrane.

13. The method of claim 12 wherein said anchoring material is selected from the group consisting of polyurethanes, silicones, bioresorbable polymers and mixtures thereof.

14. The method of claim 12 wherein said fluoropolymer membrane is ePTFE.

15. The method of claim 12 wherein said solvent is selected from group consisting of dimethylacetamide, tetrahydrofuran, ether, chloroform, methylene chloride, toluene and mixtures thereof.

16. A method of forming a stent graft assembly, the method comprising the steps of:

providing a generally cylindrical stent having an interior and an exterior, first and second ends and at least one support member;

coating at least a portion of at least one support member with a coating to substantially encapsulate at least a portion of the at least one support member;

providing at least one membrane;

placing said at least one membrane contiguous with at least a portion of at least one of the exterior and interior of the stent;

introducing a solvent in order to bond the membrane to the coating; and removing the solvent.

17. The method of claim 16 wherein the step of coating the stent is performed by spraying a polymeric solution onto the stent.

18. The method of claim 16 wherein the step of coating the stent comprises a vapor deposition process.

19. The method of claim 16 wherein the step of coating the stent comprises dipping the stent into a polymeric solution.

20. The method of claim 16 wherein the stent-graft assembly also comprises a medial region, a proximal region and a distal region, with the additional step of coating the proximal and distal regions of the stent-graft assembly.

21. The method of claim 20 wherein the step of coating the distal and proximal regions comprises dipping the proximal and distal regions of the assembly into a polymer in solution.

* * * * *

UNITED STATES PATENT AND TRADEMARK OFFICE
CERTIFICATE OF CORRECTION

PATENT NO. : 6,699,276 B2
DATED : March 2, 2004
INVENTOR(S) : Sogard et al.

It is certified that error appears in the above-identified patent and that said Letters Patent is hereby corrected as shown below:

<u>Column 1,</u>
Lines 5-6, delete "…08/721,834 filed Sep. 26, 1999 now abandoned." and insert
-- 08/721,834 filed Sep. 26, 1996 now abandoned. --

<u>Column 10,</u>
Line 4, delete "…selected from group consisting of…" and insert -- selected from the group consisting of --.

Signed and Sealed this

Eighth Day of June, 2004

JON W. DUDAS
*Acting Director of the United States Patent and Trademark Office*